(12) United States Patent
Kelley

(10) Patent No.: US 6,517,765 B1
(45) Date of Patent: Feb. 11, 2003

(54) METHOD FOR FABRICATING A FLEXIBLE AND REINFORCED TUBING

(75) Inventor: Gregory Kelley, San Diego, CA (US)

(73) Assignee: Interventional Technologies, Inc., San Diego, CA (US)

( * ) Notice: Subject to any disclaimer, the term of this patent is extended or adjusted under 35 U.S.C. 154(b) by 0 days.

(21) Appl. No.: 09/250,747

(22) Filed: Feb. 16, 1999

Related U.S. Application Data

(62) Division of application No. 08/734,682, filed on Oct. 21, 1996, now Pat. No. 5,879,342.

(51) Int. Cl.⁷ ............................................. B29C 49/22
(52) U.S. Cl. ...................................... 264/510; 264/129
(58) Field of Search ................................ 264/506, 129; 156/144, 143

(56) References Cited

U.S. PATENT DOCUMENTS

| | | | | | |
|---|---|---|---|---|---|
| 2,822,857 A | * | 2/1958 | Rothermel et al. | ......... | 156/144 |
| 3,185,182 A | * | 5/1965 | Waddell et al. | ............. | 264/506 |
| 3,294,607 A | * | 12/1966 | Rothermel et al. | ......... | 264/506 |
| 3,558,754 A | * | 1/1971 | Martin | ......................... | 264/94 |
| 3,994,761 A | * | 11/1976 | Higbee | ......................... | 156/145 |
| 4,764,324 A | * | 8/1988 | Burnham | .................... | 264/163 |
| 5,888,436 A | * | 3/1999 | Keith et al. | .................. | 264/103 |

* cited by examiner

Primary Examiner—Suzanne E. McDowell
(74) Attorney, Agent, or Firm—Scimed Life Systems, Inc.

(57) ABSTRACT

Disclosed here within is the method of manufacture of a reinforced and flexible tube or catheter that can be used in a variety of applications. The first method of embedding the metallic coil or braided wire comprises the steps of engaging the metallic structure over the outer surface of the tubular member, applying heat through an appropriately sized mold to the outer surface of the tubular member while creating a pressure differential between the inner lumen and the outside surface of the tubular member for a specified period of time. The second method of embedding the metallic coil or braided wire comprises the steps of engaging the metallic structure onto the outer surface of a mandrel, positioning the mandrel/metallic structure within the lumen of the tubular member, placing the tubular member within an appropriately sized mold, applying heat through the mold to the tubular member while creating a pressure differential between the inner lumen and the outside surface of the tubular member for a specified period of time.

8 Claims, 3 Drawing Sheets

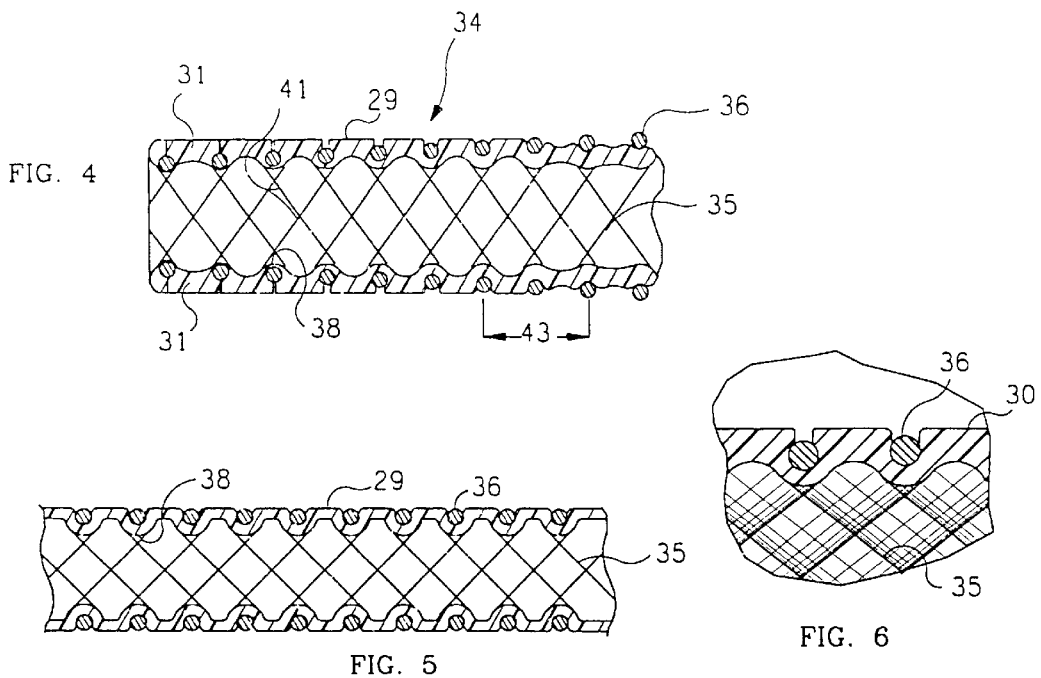
FIG. 4
FIG. 5
FIG. 6
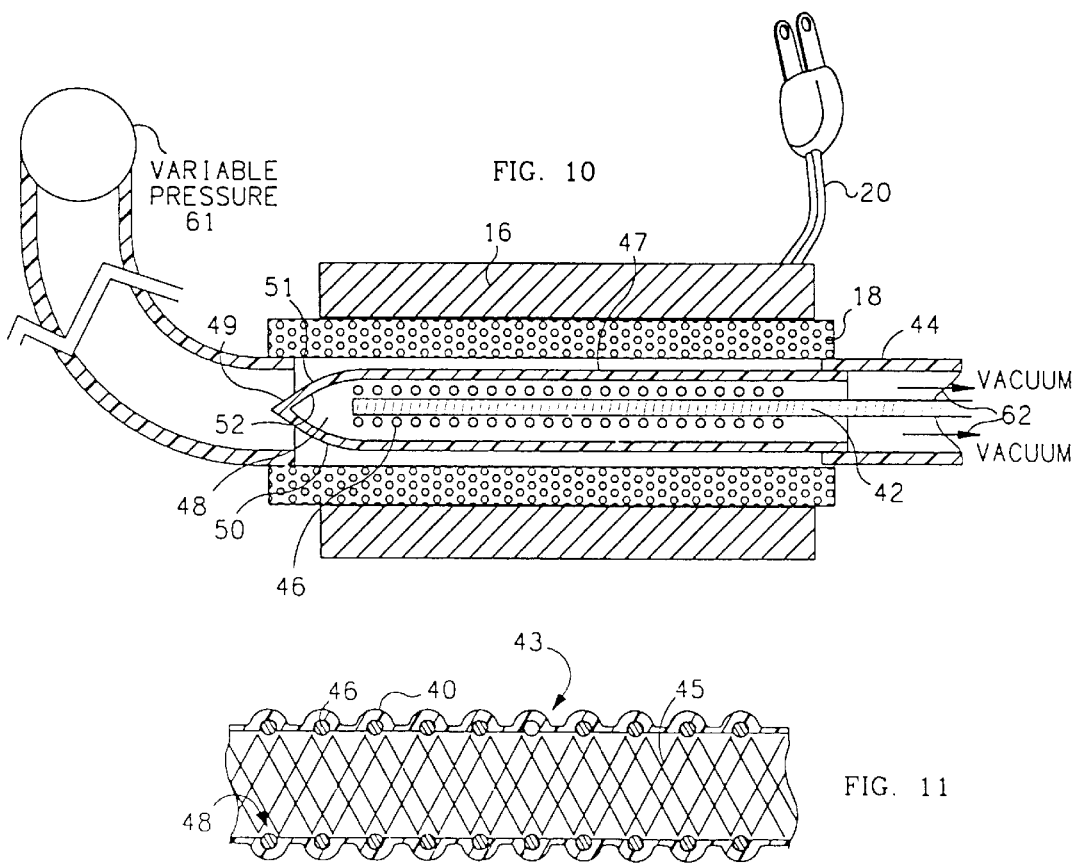
FIG. 10
FIG. 11

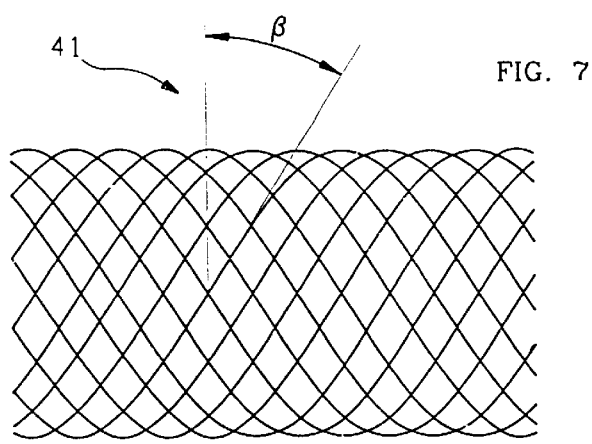
FIG. 7
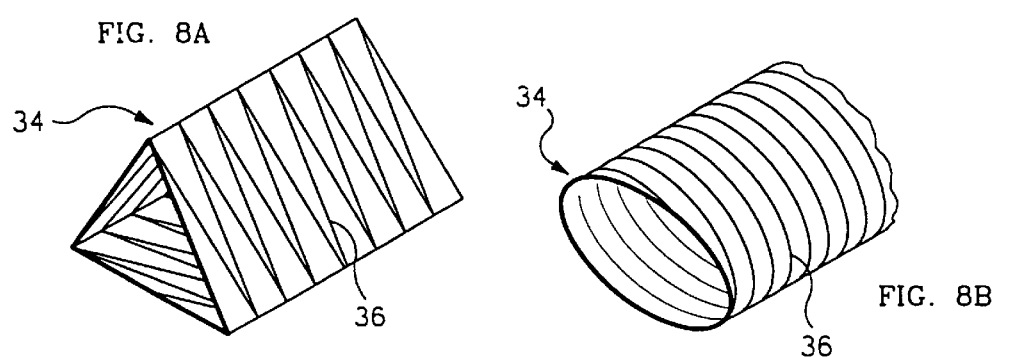
FIG. 8A
FIG. 8B
FIG. 8C
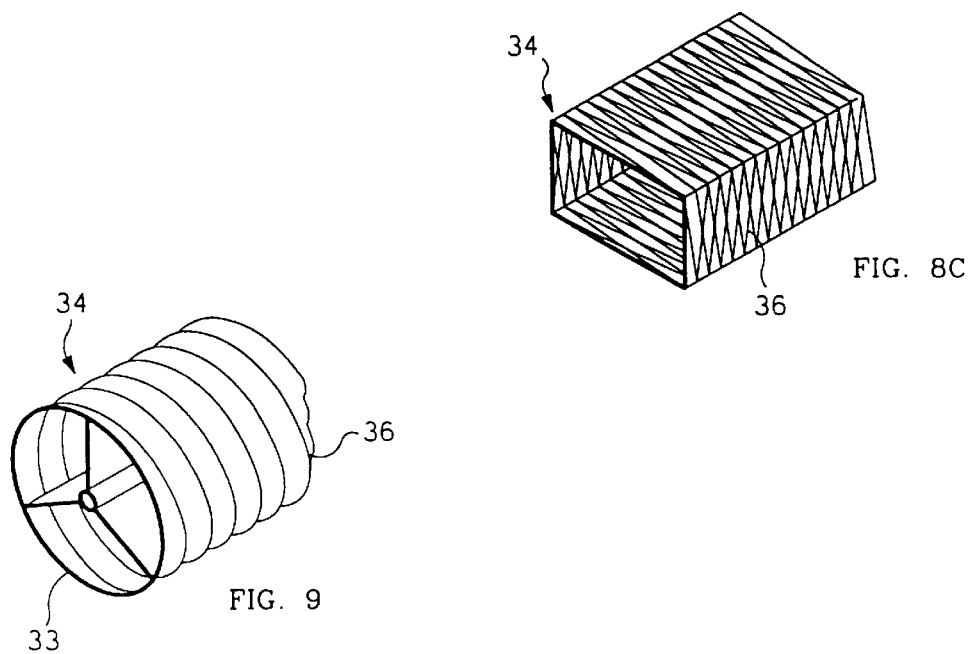
FIG. 9

METHOD FOR FABRICATING A FLEXIBLE AND REINFORCED TUBING

PRIOR APPLICATIONS

This application is a divisional of application Ser. No. 08/734,682 filed on Oct. 21, 1996, now U.S. Pat. No. 5,879,342.

FIELD OF THE INVENTION

The present invention relates to a composite tubing for use in a variety of applications and a method for manufacturing the invention. The present invention pertains to a flexible and reinforced tubing which can transmit rotational (i.e. torque) and translational (i.e. push-pull) motion. In additional, the present invention pertains to a method for manufacturing the reinforced and flexible invention. The present invention is particularly, through not exclusively, useful as a reinforced and flexible tube for use in medical applications such as a guiding catheter or a catheter with preferred torque, flexibility and pushable characteristics.

BACKGROUND OF THE INVENTION

A large number of reinforced tubing devices have been introduced for use in a wide variety of applications. For example, flexible reinforced tubing is commonly used to transmit translational motion (i.e., push-pull) or rotational motion (i.e., torque) from a control apparatus to an object located distally which is to be manipulated or moved. An example of one such device is the reinforced tubing disclosed in U.S. Pat. No. 5,101,682, which can be used in medical applications and includes a surrounding layer of electroplated material covering and bonded to the tube. Another example of a reinforced tubing device is disclosed in U.S. Pat. No. 3,769,813 for a resilient torque tube that is reinforced with alternate layers of wire net and rubber and is useful in vehicle transmissions.

Another important consideration in the design of reinforced tubing devices is the need for adequate tubing resilience (i.e., resistance to permanent deformation, kinking, and buckling under stress). Also, it may be desirable that the reinforced tubing be highly flexible for certain applications, such as for providing a conduit for fluid flow. It may also be desirable that the tubing retain sufficient strength to function effectively as a torque transmitter.

In one application, such as intravascular catheters used to advance medical devices to the arterial system surrounding the heart, there is a need for the catheter to be flexible but nevertheless, also exhibit a certain amount of stiffness so that the catheter may be advanced through various twists and turns presented by the arterial system. Also, while the body of the catheter must exhibit the desired characteristics of flexibility and stiffness, the catheter lumen must have a low friction surface so that an inner catheter or guidewire can be easily advanced through the lumen. An example of one such device which can be used in medical applications and discloses an invention which exhibits the characteristics of flexibility and stiffness is U.S. Pat. No. 5,538,510 which employs coextruded tubular members to achieve the desired results. The disadvantage of this coextrusion invention is that the manufacturing process of this device is complex and has the potential for relatively thick walls and large profiles.

While each of the reinforced tubing devices discussed above can fulfill at least one of the above requirements, there is still a need for a single reinforced tubing device which can be used interchangeably in a variety of applications and which will simultaneously provide all or several of the characteristics mentioned above. To satisfy this need, the present invention recognizes that a reinforced tubing device can be provided which is relatively strong, flexible and thin walled, and which does not easily kink, permanently deform, or buckle under stress.

Accordingly, it is an object of the present invention to provide a thin walled reinforced tubing device which is both relatively flexible and strong.

It is a further object of the present invention to provide a reinforced tubing device that efficiently transmits translational and rotational motion without easily buckling, kinking, or permanently deforming.

Yet another object of the present invention is to provide a reinforced tubing device that yields a specific inner lumen configuration which reduces the overall internal contact area and thereby reduces the frictional drag imparted to objects passing through it.

Another object of the present invention is to provide a method of reinforcing a tubular member which can vary certain properties, such as flexibility, along the length of the tubing.

Another object of the present invention is to provide a method of fabricating flexible tubing from materials not known to have flexible characteristics or from materials with a relatively high modulus.

Another object of the present invention is to provide a tubular structure containing a multitude of protruding elements which, in response to bending or flexing stresses, modify their configuration rather than and thereby minimize significant elongation and compression of the base material.

Yet another object of the present invention is to provide a reinforced tubing with relatively a thin wall and maintaining the characteristics described in the above six paragraphs.

Another object of the present invention is to provide a reinforced tubing device which can be used in a wide variety of applications.

Yet another object of the present invention is to provide a reinforced tubing device that is easy to use and relatively cost effective to manufacture.

SUMMARY

For the foregoing reasons, there is a need for a flexible, reinforced and relatively thin walled tubular member that incorporates the features described herewith and that can be inexpensively manufactured.

The present invention is directed to a tubular member that has a continuous annular wall that defines an inner lumen and at least one helical structural member that is embedded within the outer or inner surface of the tube wall. The helical coil or braided structure can be embedded to various depths; within the outer surface or inner surface of the tubular member. It is also an object of the present invention to vary the embedding depth or pitch characteristics of the helical member along any portion of a tubular member to modify the flexibility and torque characteristics over the longitudinal length of the tube. Therefore, the present invention yields a number of ridges or other shaped protrusions projecting into the lumen. These protrusions function to reduce the internal contact area and therefore reduce frictional drag when another structure is being passed through the internal lumen.

One method of manufacturing the present invention includes the steps of engaging a helical member, e.g., a braid or coil, onto the outer surface of the tubular member to form a processing composite tubular member having a first end, a second end, and at least one inner lumen. The tubular member can be either a single or multi-luminal configuration. The processing tubular member is positioned in an appropriately sized heating mold, a system to create a pressure differential is applied between the outer surface of the processing tubular member and the inner lumen by engaging a pressure source to the inner lumen of said tubular member, said processing composite tubular member is then heated to a temperature within a range for a first period of time, while either simultaneously or after a second period of time, a first pressure is applied to said lumen of said composite tubular member for a third period of time, after which said first pressure is reduced to a second pressure, and the composite tubular member is allowed to cool, resulting in a reinforced tubular structure.

Another method of manufacturing the present invention includes the steps of engaging a helical member, e.g., a braid or coil, onto the outer surface of a mandrel and positioning this helical member/mandrel assembly within the inner lumen of the tubular member forming a processing composite assembly, said processing composite assembly is then placed within an appropriately sized heating mold, a system to create a pressure differential is applied between the outer surface and the inner lumen of the tubular member by engaging a vacuum source to the inner lumen of the tubular member and supplying a pressure source to the outer surface of the tubular member or, said processing composite assembly is then heated to a temperature within a range for a first period of time while either simultaneously or after a second period of time, the pressure differential is created by applying a first pressure to the outer surface of the tubular member and a first vacuum to the inner lumen of the tubular member, said pressure differential is applied for a third period of time, after which the pressure differential is reduced to a null, and said composite tubular member allowed to cool, resulting in a processed composite tubular member.

During the fabrication process, the mold can be shaped such that the processed reinforced tubular member is final configured with one or more radii. in addition, the mold can be configured such that the processed reinforced tubular member yields a substantially circular, oval, triangular# or other geometric shape in cross section.

After the reinforced tube is processed, either the outer surface, the inner surface, or both surfaces, can be coated with a suitable material.

BRIEF DESCRIPTION OF THE DRAWINGS

FIG. 4 is a sectional view showing the processed reinforced tubing with the helical member embedded in various depths within the tubular member.

FIG. 5 is a sectional view showing the reinforced tubing with the helical member embedded in a fixed depth into the tubular member and demonstrating the multiple convex ridges protruding into the lumen.

FIG. 6 is an magnified sectional view showing the relationship of the tubular member with the embedded helical member, e.g., a braid or coil;

FIG. 7 is a side elevational view showing the method of calculating the pitch angle of the helical member.

FIGS. 8a, 8b, and 8c are side elevational views showing the reinforced tubing in a triangular (8a), oval (8b) and square (8c) configuration.

FIG. 9 is a side elevation view of the multiple lumen design of the reinforced tubing.

FIG. 10 is a sectional view showing the tubular member with a helical member, e.g., a coil or braid, engaged to a mandrel and positioned within the lumen of the tubular member forming a processing structure which is positioned within a thermal source and connected to pressure differential sources.

FIG. 11 is a sectional view showing the reinforced tubing with the coil or braid embedded in a fixed depth into the tubular member and demonstrating the multiple convex ridges protruding into the lumen and projecting out from the outer surface.

DESCRIPTION OF THE PREFERRED EMBODIMENTS

Figure 1:
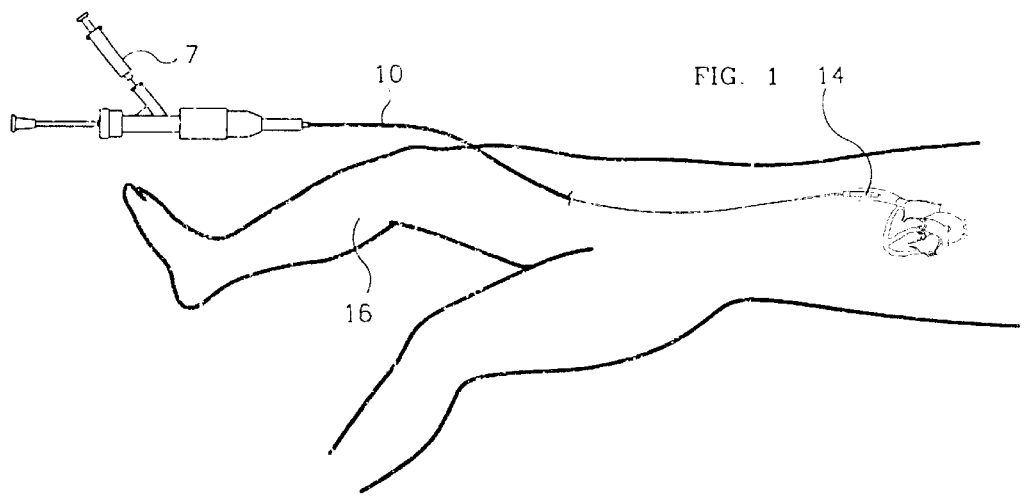
FIG. 1 is a perspective view of the novel reinforced tubing in one intended environment, showing the tubing positioned in an artery and in operative association with a balloon catheter device.

Initially referring to FIG. 1, it can be seen that a reinforced tubing, generally designated 10, may be operatively associated with various ancillary devices in various diverse applications. For example, FIG. 1 shows tubing 10 operatively associated with an angioplasty inflation/deflation apparatus 7 and an expandable angioplasty balloon 14. In the application of tubing 10 shown in FIG. 1, tubing 10 is a guiding catheter for providing access from the femoral artery to the coronary vasculature to balloon catheter 14. In this application, the tubing 10 must be flexible to minimize damage to the aorta and possess transmitting torque capability to position the tip of the guiding catheter to the orifice of a coronary artery. Tubing 10 is also a conduit for communicating fluid to the coronary artery once properly positioned. While FIG. 1 illustrates one potential application of tubing 10, it is to be understood that the application shown in FIG. 1 is merely exemplary. As a further example of a potential application for this invention, tubing 10 could be used as a connector between a fluid source and a fluid receiver for fluid communication applications requiring a strong, relatively thin walled yet flexible hose connector, or as a control cable and fluid conduit in a surgical atherectomy apparatus.

Figure 2:
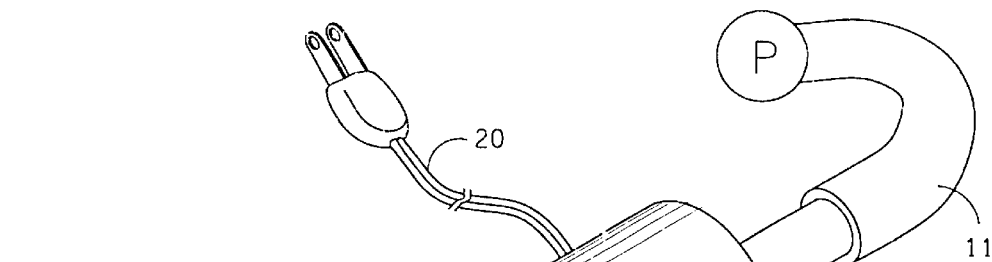
FIG. 2 is a perspective/sectional view showing the tubular member with the helical member, e.g., a coil or braid, in contact with the outer surface of the tubular member and positioned within a thermal source, and the lumen of the tubular member engaged with a pressure source.
Figure 3:
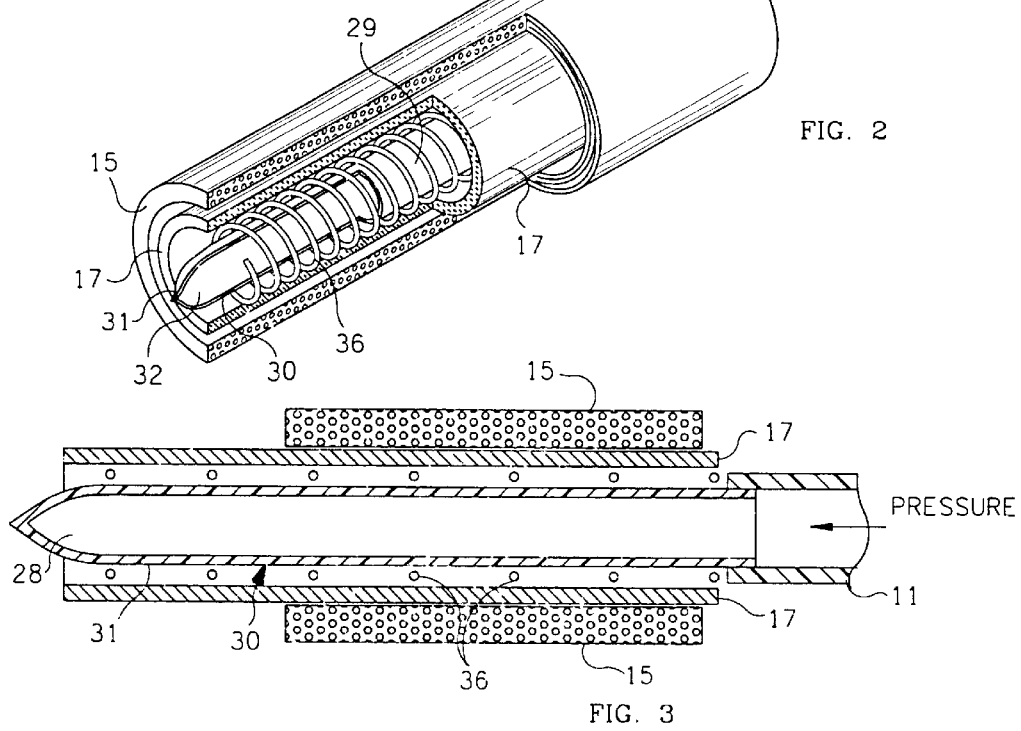
FIG. 3 is a sectional view showing the tubular member with the helical member in contact with the outer surface of the tubular member forming a pre-processed composite tubular member, the lumen of the tubular member engaged with a pressure source and the pre-processed composite tubular member positioned within a thermal source.

Turning now to FIGS. 2 and 3, the details of preprocessed reinforced tubing 10 can be seen. There, tubing 10 is shown to include a hollow tubular member 30 in juxtaposition with the helical member (braid or coil) 36 to form a pre-processed tubular composite. FIGS. 2 and 3 also shows a processing mold 17 which is in contact with thermal source (heater) 15 and which is in juxtaposition with the pre-process tubular composite. Also shown is a representation of a temperature control system 20 and a variable pressure source 11.

As best shown in FIGS. 2 and 3, the pre-processed tubular member has a continuous, substantially cylindrical annular wall 31 which defines an inner surface 32 and an outer surface 29. Wall 31 of tubular member 30 also defines a central hollow lumen or passageway 28, through which liquid or gas can flow in connection with, for example, angioplasty surgery applications of tubing 10. Importantly, the dimensions of tube 30 (and tubing 10) may be established as appropriate for the particular application of tubing 10. It is to be understood, however, that the outer diameter, the inside diameter and the thickness of the wall 31 of tube 30 may be adjusted to meet the criteria of an appropriate application. Furthermore, the length of tubing 10 may be established as appropriate for the particular application of tubing 10. For example, tubing 10 may have a length which can vary between a few inches and several yards.

Additionally, tube 30 is preferably made of strong yet flexible polymeric materials, such as polyamide, polybutylone terephthalate, polyetherimide, polyethylene, polyethylene terephthalate, polyethylene napthalate, or any combinations thereof. It is not essential that the, base polymeric material have flexible characteristics or have a low modulus. The process disclosed herein will tender a high modulus, inflexible base material to have characteristics which in the present invention, greatly exceeds the flexibility of a tubular member that is merely extruded using such a base material. As the skilled artisan will appreciate, the material of tube 30 may also be selected to be compatible with the particular application of tubing 10. For example, certain applications of tubing 10 may dictate that the material of tube 30 be chemically compatible with certain fluids which may be communicated through passageway 28 of tube 30, and further that the material of tube 30 be nontoxic and nonoxidizin4.

Furthermore, tubular member can comprise a multiple lumen configuration (FIG. 9). The multiple lumen configuration will have the thin wall, flexible and reinforced characteristics similar to the single lumen design yet have an assortment of lumens where each lumen can have a different and independent function.

Referring to FIGS. 2 and 3 demonstrating the pre-processed composite member and FIG. 4 demonstrating the post-processing configuration, the helical member 36 is shown in juxtaposition to outer surface 29 of tubular member 30. More particularly, as shown in FIG. 4, helical member 36 is positioned on tubular member 30 to form a succession of spaced apart coils 43 whose respective edges do not contact each other. Also, although the present invention uses a wire for helical member 36, it is to be understood that the geometry of helical member 36 may be any geometry suitable for providing structural support for tube wall 31, such as a flat ribbon or triangular configuration. Importantly, helical member 36, should be made of a material which, when helically is juxtaposition to the outside surface of tubular member 30, provides sufficient hoop strength to structurally strengthen tube wall 31. In the present invention helical member 36 is composed of tungsten or stainless steel, but it is to be understood that other materials may be used which fulfill the strength and bonding requirements discussed above, such as molybdenum, cobalt, nickel, or combinations thereof It is also within the scope of this invention that non-metallic materials may be employed as the helical member 36, such as nylon, carbon or boron fibers, or aromatic polyamide fibers (e.g. Kevlar®).

In addition to the material requirements of helical member 36 disclosed above, it will be recognized by the skilled artisan that the dimensions and configuration of member 36 will have a significant effect on the operational capabilities of tubing 10. On the one hand, these variables must be selected to provide sufficient structural support for tube wall 31. on the other hand, (for certain applications of tubing 10) the variables must be selected to minimize the wall thickness of tubing 10. For example, when tubing 10 is to be used in the angioplasty surgery application shown in FIG. 1, thickness of helical member 36 may range from one half thousandth (0.0005")of an inch to twelve thousandth (0.012") of an inch, preferably ranging from one to four thousandths (0.001"–0.004") of an inch in diameter. The is preferred range is desirable in human clinical applications to minimize the profile or overall outside diameter while maximizing the lumen diameter of the device to match dimensional limitations of the human vasculature. For other applications which require even greater strength of tubing 10, helical member 36 may be relatively thicker.

As the skilled artisan will also readily appreciate, an angular pitch 41 between the successive coils 43 of helical member 36, can be selected to provide for flexibility as well as for sufficient torque transmission characteristics in tubing 10. In fact, the present invention envisions a pitch angle 41 (defined as the angle between a line perpendicular to the longitudinal axis and the slope of one of the coil or braid stands) along the length of tubing 10 which can be varied between one (1) degree and ninety (90) degrees, preferably between five (5) and forty five (45) degrees, 40 flexibility and torque transmission requirements dictate. For example, pitch angle 41 may be relatively high (about forty five (45) degrees) at one end of tubing 10 for maximum tor a transmission. Pitch 41 may then be gradually or suddenly decreased to about five (5) degrees at the second end of tubing 10 to provide for more flexibility of tubing 10 near either end or varied along its length.

In one method of manufacturing the embodiment shown in FIGS. 4, 5 and 6, helical member 36 becomes embedded, from the outer surface 29, into tube wall 31. Initially, helical member 36, being a braid or coil, is engaged onto the outer surface 29 of the tubular member 30 to form a preprocessed composite tubular member having a first end, a second end, and an inner lumen. Then, the pre-process composite is positioned in an appropriately sized heating mold 17, whereby a pressure source is engaged to the inner lumen 28 of tubular member 30. Heat is applied to the composite tubular member using a temperature range for a specified period of time. Typically the temperature range is dependent on the polymeric material employed, and may range anywhere from 100 degrees Fahrenheit to 880 degrees Fahrenheit depending on the polymeric material. When tubing 10 is being used as a guiding catheter and the polybutylene terephthalate material is employed, the preferable range is from 350 degrees Fahrenheit to 420 degrees Fahrenheit. In an another embodiment, for example, when tubing 10 is being used as a torque tube in medical applications and the polyamide material is employed, the preferable range is from 275 degrees Fahrenheit to 350 degrees Fahrenheit. Since various polymeric materials could be utilized in this process, the temperature range is dependent on, and therefore adjusted for, the polymeric material employed.

Either simultaneously or after a predetermined time period has passed, a first pressure is applied to the lumen 28 of the composite tubular member 30 to cause the pressure differential across the tube wall. Typically the pressure range is dependent on the diameter and wall thickness of the tubular member employed, and therefore may range anywhere from 20 psi to 5000 psi depending on specific parameters of the tube. When tubing 10 is being used as a guiding catheter and the polybutylene terephthalate material is employed, the preferable range is from 300 psi to 550 psi. in an another embodiment, for example, when tubing 10 is being used as a torque tube in medical applications and the polyamide material is employed, the preferable range is from 450 psi to 650 psi. Since a wide range of tubular diameter and wall thickness could be utilized in this process, the pressure range is dependent on these parameters.

After the processing time has expired, the first pressure is reduced to a second pressure. Finally the composite is tubular member 30 allowed to cool resulting in a processed reinforced tubing 34.

It is to be appreciated that the processed structure disclosed above results in the braid or coil member 36 becoming embedded into the wall 31 of processed tubular member 34. As the skilled artisan will also readily appreciate and as demonstrated on FIG. 4, the temperature, pressure or time can be adjusted during the process to result in varying the depth of which the coil or braid 36 becomes embedded in wall 31 of processed tubular member 34. These process parameters may then be gradually or suddenly reduced or increased along the length of the tubular member to result in various depths that the coil or braid becomes embedded. Furthermore, as the braid or coil member 36 becomes embedded into the wall 31, one or more projecting elements protrude from the inner surface 32 of tubular structure 30. such elements 38, as shows in FIGS. 4 and 5, result in a ridge which conforms to and surrounds the embedded helical member. It is also possible that these elements can be formed in a specific configuration, such as a parallelogram, trapezoid or triangle.

Importantly, the dimensions of tubular member 30 (and tubing 10) may be established as appropriate for a number of applications which result in the formation of particular tubular member. For example, when tubing 10 is being used As a guiding catheter for angioplasty applications, inner diameter of tube 30 may range from approximately thirty nine thousandth (0.039") of an inch to four hundred and forty five thousandth (0.445") of an inch, preferably from sixty thousandth (0.060") of an inch to one hundred and twenty five thousandth (0.125") of an inch, and the outside diameter of tube 30 may range from fifty three thousandth (0.053") of an inch to four hundred and fifty eight (0.458") of an inch, preferably from seventy nine thousandth (0.079") of an inch to one hundred and forty four thousandth (0.144") of an inch. The preferred inside and outside diameters are appropriate for currently marketed angioplasty and interventional devices that would be used with the guiding catheter application.

In another embodiment, for example, when tubing 10 is being used as a torque tube in medical applications, inner diameter of tube 30 may range from approximately twelve thousandth (0.012") of an inch to four hundred and forty five thousandth (0.445") of an inch, preferably from forty thousandth (0.040") of an inch to seventy thousandth (0.070") of an inch, and the outside diameter of tube 30 may range from sixteen thousandth (0.016") of an inch to four hundred and fifty eight thousandth (0.458") of an inch, preferably from fifty two thousandth (0.052") of an inch to ninety thousandth (0.090") of an inch. The preferred diameters are appropriate for 30 currently marketed angioplasty and interventional devices.

It is to be understood that the processed structure disclosed above results in several advantages. First, tubing 10 is a flexible yet strong hollow and relatively thin walled tube which can effectively transmit both translational motion and rotational motion (i.e., torque). Thus, tubing 10 can be used as A control cable or torque conveyor in a variety of applications. Second, the structure disclosed above results in a tubing 10 which will not readily kink or permanently deform when bent. Third, tubing 10 will not readily buckle under tensile or compressive stress, such as what may be generated when tubing 10 is being used to transmit translational and/or rotational motion. Fourth, the present invention does not require materials known to have flexible characteristics or materials with a low modulus. Fifth, the present invention provides a tubular structure containing a multitude of protruding elements which, in response to bending or flexing stresses, modify their configuration and thereby minimize significant elongation and compression of the base material. Sixth, the present invention provides a reinforce tubing device that yields a specific inner lumen configuration which reduces the overall internal contact area and thereby reduces the frictional drag imparted to objects passing through the lumen.

Certain applications of tubing 10 may require that a coating (not shown) be applied to the outer surface 33 of the processed composite tubing 34. Suitable materials for such a coating can be polyetherimide, polyethylene, polyurethane, silicone products, parylene, or lubricous hydrophilic coatings.

In a second method of manufacturing the embodiment shown in FIGS. 10 and 11, helical member 46 becomes embedded into tube wall 51 of tubular member 50 through the inner surface 52. Tubular member 50 is defined by having a first end, a second end, and an inner lumen 48. Initially, a helical member 46 e.g., braid is engaged onto the exterior surface of mandrel 42 which is positioned and centered within lumen 48 of tubular member 50. The preprocess composite is then positioned in an appropriately sized heating mold 18. A system for creating a pressure differential is applied between the outer surface 49 and the inner lumen 48, by engaging a vacuum source 62 to the inner lumen 48 of tubular member 50 and applying a pressure source to the outer surface 49 of tubular member 50. As shown in FIG. 10, heating mold 18 is connected to a variable pressure source 61 to create a pressure which engages the outer surface 49 of tubular member 50. A spacer 44 functions to seal the second end of heating mold 18. As a skilled artisan can appreciate, several methods of obtaining a pressure differential between the inner lumen 48 and outer surface 49 (across the wall) of the tubular member 50 are available. Heat is applied from mold 18 to the composite tubular member into a temperature range for a first period of time. Either simultaneously or after a second time period, the pressure differential is created by applying a first pressure to the outer surface of the composite tubular member 50 and a first vacuum to the inner lumen of the composite tubular member 50. After the processing times have expired, the pressure differential is reduced to a null and the composite tubular member 50 is allowed to cool. The mandrel is removed, resulting in a processed reinforced tubing 53.

It is to be understood that the processed structure disclosed above results in the braid or coil member 46 embedded through the inner surface 52 and into the wall 51 of tubular member 50. As the skilled artisan will also readily appreciate, the temperature, vacuum, pressure or time can be adjusted during the process to result in varying the depth of which coil or braid 46 becomes embedded in wall 51 of tubular member 50. These process parameters may then be gradually or suddenly reduced or increased along the length of the tubular member to result in various depths that the coil or braid becomes embedded.

The details of the operation of tubing 10 will vary according to the particular application of tubing 10. When tubing 10 is to be used as a torque transmitter/control cable, tubing 10 is operatively associated with the particular control apparatus being used, such as the apparatus 7 shown in FIG. 1, or a motor throttle (not shown) or even a person's hand (not shown). Distal end of tubing 10, in contrast, can be attached to the, mechanism being manipulated, such as the angioplasty balloon 14 shown in FIG. 1. Translational motion and torque may then be transmitted through tubing 10 from the particular Control apparatus being used to the mechanism being manipulated. At the same time, because tube 30 is hollow, fluid or gas may be communicated between the proximal end and the distal of tubing 10.

While the particular reinforced tubing as herein shown and disclosed in detail is fully capable of obtaining the objects and providing the advantages herein before stated, it is to be understood that it is merely illustrative of the presently preferred embodiments of the invention and that to limitations are intended to the details of construction or design herein shown other than as described in the appended claims.

I claim:

1. A method for reinforcing a tubular structure for medical devices which comprises the steps of:
   (a) engaging at least one helical member onto an outer surface of a tubular member to form a composite tubular assembly having a first, a second end, and an inner lumen;
   (b) positioning said composite tubular assembly in a heating mold;
   (c) heating said composite tubular assembly into a temperature range, said temperature range being between a first temperature and a second temperature;
   (d) creating a pressure differential between said outer surface and said inner lumen;
   (e) reducing said pressure differential;
   (f) removing said composite tubular assembly from said heating mold to result in a reinforced tubular structure; and
   (g) applying a coating on an inner surface of said reinforced tubular structure.

2. A method as recited in claim 1 further comprising the steps of: applying a coating on said outer surface of said reinforced tubular structure.

3. A method as recited in claim 1 wherein said heating mold is configured such that said reinforced tubular structure results in having one or more radii.

4. A method as recited in claim 1 wherein said reinforced tubular structure is oval, triangular, or square in cross section.

5. A method for reinforcing a tubular structure for medical devices which comprises the steps of:
   (a) engaging at least one helical member onto a mandrel to form a processing assembly;
   (b) positioning said processing assembly inside a tubular member to form a composite tubular assembly, said tubular member having an outer surface, an inner surface and an inner lumen;
   (c) positioning said composite tubular assembly in a heating mold;
   (d) heating said composite tubular assembly into a temperature range, said temperature range being between a first temperature and a second temperature;
   (e) creating a pressure differential between said outer surface of said tubular member and said inner lumen of said tubular member;
   (f) reducing said pressure differential;
   (g) removing said composite tubular assembly from said heating mold to result in a reinforced tubular structure; and
   (h) applying a coating on an inner surface of said reinforced tubular structure.

6. A method as recited in claim 5 further comprising the steps of applying a coating on the outer surface of said reinforced tubular structure.

7. A method as recited in claim 5 wherein said reinforced tubular structure results in having one or more radii.

8. A method as recited in claim 5 wherein said reinforced tubular structure results in having an oval, triangular, or square cross section.

* * * * *